May 9, 1972 R. G. JELLY Plant Pat. 3,167
HYBRID TEA ROSE
Filed Oct. 24, 1969
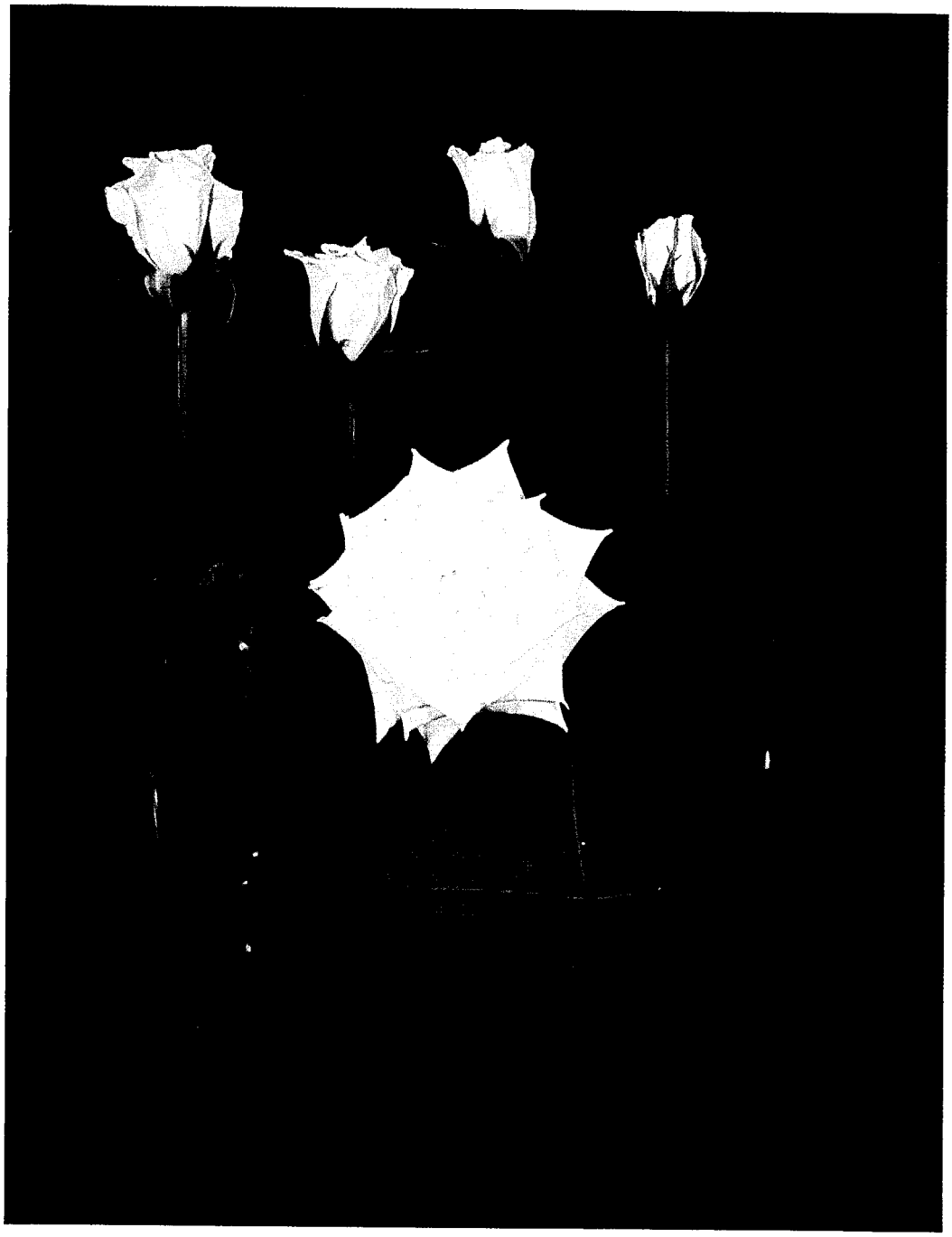
INVENTOR.
ROBERT G. JELLY
BY Rummler & Snow
ATTYS.

United States Patent Office

Plant Pat. 3,167
Patented May 9, 1972

3,167

HYBRID TEA ROSE

Robert G. Jelly, Richmond, Ind., assignor to
E. G. Hill Co., Inc., Richmond, Ind.

Filed Oct. 24, 1969, Ser. No. 869,403
Int. Cl. A01h *5/00*
U.S. Cl. Plt.—14 1 Claim

ABSTRACT OF THE DISCLOSURE

A new variety of hybrid tea rose plant developed for greenhouse production of cut flowers by cross with Snowsong Supreme (P.P. 2,624) and distinguished by longer stems for its blooms, the lively white color of the blooms, and the ability of the flowers to withstand handling and shipping without bruising.

BACKGROUND OF THE INVENTION

This new variety of rose plant is the result of breeding efforts carried on by me at Richmond, Ind., with the object of producing a white hybrid tea rose that would overcome the problems usually found in the commercial production and distribution of greenhouse grown white roses, namely botrytis susceptibility and the failure to withstand normal handling and shipping conditions without spoilage. My objective was accomplished by crossing Snowsong Supreme (P.P. 2,624), known for its vigorous growth and excellent flower productivity under greenhouse culture, its distinctive white flowers of classic form, and its good year around color retention, with an unnamed white seedling used as a parent because of its excellent growth habits and keeping qualities and in spite of its tendency as a cut flower to fail to fully open in a vase.

I found that the seedling resulting from this cross of Snowsong Supreme and the said unnamed white seedling as the pollen parent not only obtained the excellent growth habits and keeping qualities of the pollen parent but also the good characteristics of the seed parent plus longer stems for its singly borne blooms, a marked increase in vase life, and an ability to withstand high temperatures, with less decrease in bloom size.

Asexual propagation of this new variety, through many generations following the first flowering in March 1965 from a crossing done in October 1964, carried on under my direction at Richmond, Ind., by grafting and at Livermore, Calif., by budding, has demonstrated conclusively that the distinguishing characteristics of the new variety are fixed and hold true in all respects.

DESCRIPTION OF THE DRAWING

This new variety of rose plant is illustrated by the accompanying photographic representation in which typical specimens of the bud in various stages of opening, from the time the sepals divide, are shown with a face view of a fully opened flower, upper and underside views of mature leaves, a typical piece of the mature wood, and a piece of new wood with young leaf.

DESCRIPTION OF THE NEW PLANT

The following is a detailed description of my new variety of white tea rose plant with color designations according to Robert S. Wilson's "Horticultural Colour Chart," Koster's "Color Guide," and Nickerson's "Color Fan," identified as (W), (K), and (N), respectively.

*The plant*

Origin: Seedling (#62–65W).
Parentage:
*Seed parent.*—Snowsong Supreme (P.P. 2,624)

*Pollen parent.*—An unnamed and unpatented white seedling #16–59W.
Classification: Hybrid tea.
Type: Greenhouse growing for cut flower production (tested negative for garden use).
Form: Bush.
Growth: Moderately free and vigorous.
Habit: Upright and much branched with canes of medium diameter.
Main stems: Color—Cedar Green, Plate 80 (K).
*Thorns.*—Few, short and hooked slightly downward with a short, narrow base.
*Color of thorns.*—Fawn Brown, Plate 89 (K).
*Prickles and hairs.*—None.
Branches: Color—Moderate Olive Green, 7.5GY4/4 (N).
*Thorns.*—Few. short to medium length with a short and narrow base.
*Color of thorns.*—Slightly lighter than strong Greenish yellow, 7.5Y7/9.
*Prickles and hairs.*—None.
Foliage:
*Leaves.*—Shape—odd pinnate (compound)—size—medium, moderately thick.
*Leaflets.*—3 to 7 in number. Shape—elliptical with cuspidate apex, obtuse base, and serrate margin—Color—young upper surface—Parsley Green 00962/2 (W) with main vein and leaf edges Dark Red 5R3/7 (N)—young under surface—Sedar Green, Plate 80 (K) suffused with Dark Red 5R3/7 (N)—mature upper surface—slightly greener than Parsley Green 00962/3 (W)—mature under surface—slightly greener than Lavender Green 00761 (W).
*Rachis.*—Light to medium—upper side—grooved, with minute prickles—under side—an occasional prickle.
*Stipules.*—Moderately short, narrow, turning out at an angle of less than 45 degrees, and with points which are of short to medium length.

*The bud*

Form:
*Before calyx breaks.*—Short pointed, with a conspicuous neck. Bud has foliaceous appendages on its surface and slender bristle-like foliaceous parts extending beyond the bud tip a distance of about one-fourth or more of the bud length.
*As first petals open.*—Short pointed.
Size: Medium large, before calyx breaks and as first petals open.
Character of opening: Opens well in greenhouse. In extremely warm weather, the bud size will decrease slightly and in extremely cold, cloudy weather, the green venation increases in intensity.
Color:
*Calyx.*—Shaded from Scheeles Green 860 (W) at base to slightly darker than Scheeles Green 860/2 (W).
*Petals.*—As calyx breaks and as first petal opens: outside—Uranium Green 63/3 (W) with venation of strong Yellow Green 2.5GY6/8 (N)—inside—Uranium Green 63/3 (W) with venetion of strong Yellow Green 2.5GY6/8 (N).
Peduncle: Medium diameter and length, erect and strong.
Bark: Slightly rough. Color—From Spanish Green 0960/3 (W) to slightly lighter than Spanish Green.
Thorns: None—prickles—numerous; color—Mimosa Yellow 602/2 (W).
Hairs: None.

*The flower*

Blooming habit: Continuous and free in greenhouse.

Size: Medium large, when fully open, 4 to 5 inches in diameter.

Form: Full and high centered, at first, becoming flat to slightly high centered as bloom matures.

Borne: Singly, on moderately strong, medium length to long stems.

Petalage: Number of petals—40 to 48, stamens not hidden.

*Arrangement.*—Regular, petals remaining tightly rolled outward as bloom matures.

*Shape.*—*Outside petals*—oval, apex almost entire with one slight notch. *Intermediate petals*—oval, apex almost entire with one slight notch, some petals being entire. *Inside petals*—oval, apex with one prominent notch.

*Color.*—Colors may be modified by being shaded with other colors; bloom also has venation variation.

The following is from a newly-opened flower grown in greenhouse at Richmond, Ind., and first blooming in March 1969:

*Outside petals and intermediate petals.*—Outside surface, white with a Uranium Green 63/2 (W) base; inside surface, white with a brilliant Yellow Green 2.5GY9/8 (N) base.

*Inner petals.*—Outside surface, shaded from Chartreuse Green 663/3 (W) to Chartreuse Green 663/2 (W) at base; inside surface, shaded from Chartreuse Green 663/3 (W) to Chartreuse Green 663/2 (W) at base.

The following is from a rose opened for three days in greenhouse at Richmond, Ind., in March 1969:

*Outside petals.*—Outside surface, white with petal base brilliant Greenish Yellow 10Y9/9 (N); inside surface, white with petal base slightly lighter than brillant Yellow Green 2.5GY9/8 (N).

*Intermediate petals.*—Outside and inside surfaces, white with petal base brilliant Yellow Green 2.5GY9/8 (N).

*Inner petals.*—Outside and inside surfaces, white with petal base Chartreuse Green 663/2 (W).

General color effect:

*Newly opened flower.*—White with a cast of Chartreuse Green 663/3 (W).

*Three days opened flower.*—White with a cast of slightly lighter than Primrose Yellow 601/3 (W).

Texture: Moderately leathery.

Appearance: Inside—satiny; Outside—flat (not shiny or satiny).

Calyx tube: Short to medium length with conspicuous neck; funnel-shaped, with very smooth walls.

Sepals: Permanent, medium length. Color—Inside—Lavender Green 000761 (W) to Pod Green 061/2 (W)—outside—shaded from Spinach Green 0960/3 (W) to Pod Green 061/1 (W) with a distinct pubescent margin.

Stem: Longer than seed parent, erect and moderately strong.

Fragrance: Slight—sweetbriar (in greenhouse).

Persistence: Petals persist in greenhouse.

Effect of weather: In hot, humid weather, there is a rapid deterioration of the petals and the blooms fade to a lighter than Primrose Yellow 601/3 (W).

Lasting quality: 10 days in March—for cut roses grown in greenhouse and kept at living room temperatures.

*Reproductive organs*

Stamens: Medium number, arranged irregularly about pistils, some mixed with petaloids.

*Anthers.*—Medium, open at various times. Color—Apricot, Plate 11 (K).

*Filaments.*—Short, most with anthers. Color—varies from Sap Green 62/2 (W) to slightly darker than Sap Green 62/3 (W).

*Pollen.*—Moderate. Color—a little lighter than Orange, Plate 12 (K).

Pistils: Many in number.

*Styles.*—Uneven, short to medium length, moderately thin, loosely bunched. Color—Sap Green 62/3 (W).

*Stigmas.*—Color—Sap Green 62/3 (W).

Ovaries: Almost all encased in calyx.

Hips: Thin and fleshy.

Seeds: Many of medium size.

This variety is an improvement over its seed parent, Snowsong Supreme (P.P. 2,624), in that it withstands high temperatures with less decrease in bloom size and because the blooms are borne on longer stems and have a marked increase in vase life. Although the pollen parent (16–59W) had a major drawback in that it did not always open fully, as a cut flower, in a vase, it was used as a parent for the new variety because of its excellent growth habits and keeping qualities which were transmitted to the new seedling and were important factors in the selection of the new seedling for testing to prove its advantages for commercial exploitation. The result is a new variety of white tea rose plant that fully meets the objectives for which the new variety was sought and which provides a bloom having a lively white color, due to its green base, a high degree of resistance to bruising, and an exceptional vase life.

I claim:

1. A new and distinct variety of rose plant substantially as herein shown and described, characterized by its lack of botrytis susceptibility, its continuous production of lively white blooms, under greenhouse culture, which are borne on long to medium long straight stems and which are highly resistant to bruising during normal handling and shipping operations.

No references cited.

ROBERT E. BAGWILL, Primary Examiner